(12) United States Patent
Burton et al.

(10) Patent No.: US 8,292,912 B2
(45) Date of Patent: Oct. 23, 2012

(54) BALLOON CATHETER THAT RESISTS CURVING

(75) Inventors: David G. Burton, Bloomington, IN (US); Scott E. Boatman, Bloomington, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 1272 days.

(21) Appl. No.: 11/450,912

(22) Filed: Jun. 9, 2006

(65) Prior Publication Data

US 2006/0287665 A1    Dec. 21, 2006

Related U.S. Application Data

(60) Provisional application No. 60/689,451, filed on Jun. 10, 2005.

(51) Int. Cl.
*A61M 29/00* (2006.01)
(52) U.S. Cl. ...................................................... 606/194
(58) Field of Classification Search .......... 606/191–194; 623/1.11; 604/96.01, 103.12, 103
See application file for complete search history.

(56) References Cited

U.S. PATENT DOCUMENTS

| | | | |
|---|---|---|---|
| 4,998,923 A | 3/1991 | Samson et al. | 606/194 |
| 5,171,221 A | 12/1992 | Samson | 604/96 |
| 5,549,552 A * | 8/1996 | Peters et al. | 604/103.1 |
| 5,782,809 A | 7/1998 | Umeno et al. | 604/280 |
| 6,706,010 B1 * | 3/2004 | Miki et al. | 604/43 |
| 8,114,048 B2 * | 2/2012 | Pagel et al. | 604/96.01 |
| 2003/0114911 A1 * | 6/2003 | Lupton | 623/1.11 |
| 2009/0036829 A1 * | 2/2009 | Pagel et al. | 604/96.01 |

FOREIGN PATENT DOCUMENTS
WO    WO 96/38193    12/1996

OTHER PUBLICATIONS

International Search Report for PCT/US2006/022504, dated Oct. 10, 2006, 12 pages.

* cited by examiner

*Primary Examiner* — Gary Jackson
*Assistant Examiner* — Eric Blatt
(74) *Attorney, Agent, or Firm* — Brinks Hofer Gilson & Lione

(57) ABSTRACT

A balloon catheter is provided to minimize curving of the balloon when the balloon is expanded with an inflation media. The balloon catheter has an elastic inner shaft that stretches longitudinally as inflation pressure in the balloon is increased. The balloon catheter may also have an inner shaft with a portion that is corrugated to allow longitudinal stretching of the inner shaft.

19 Claims, 3 Drawing Sheets

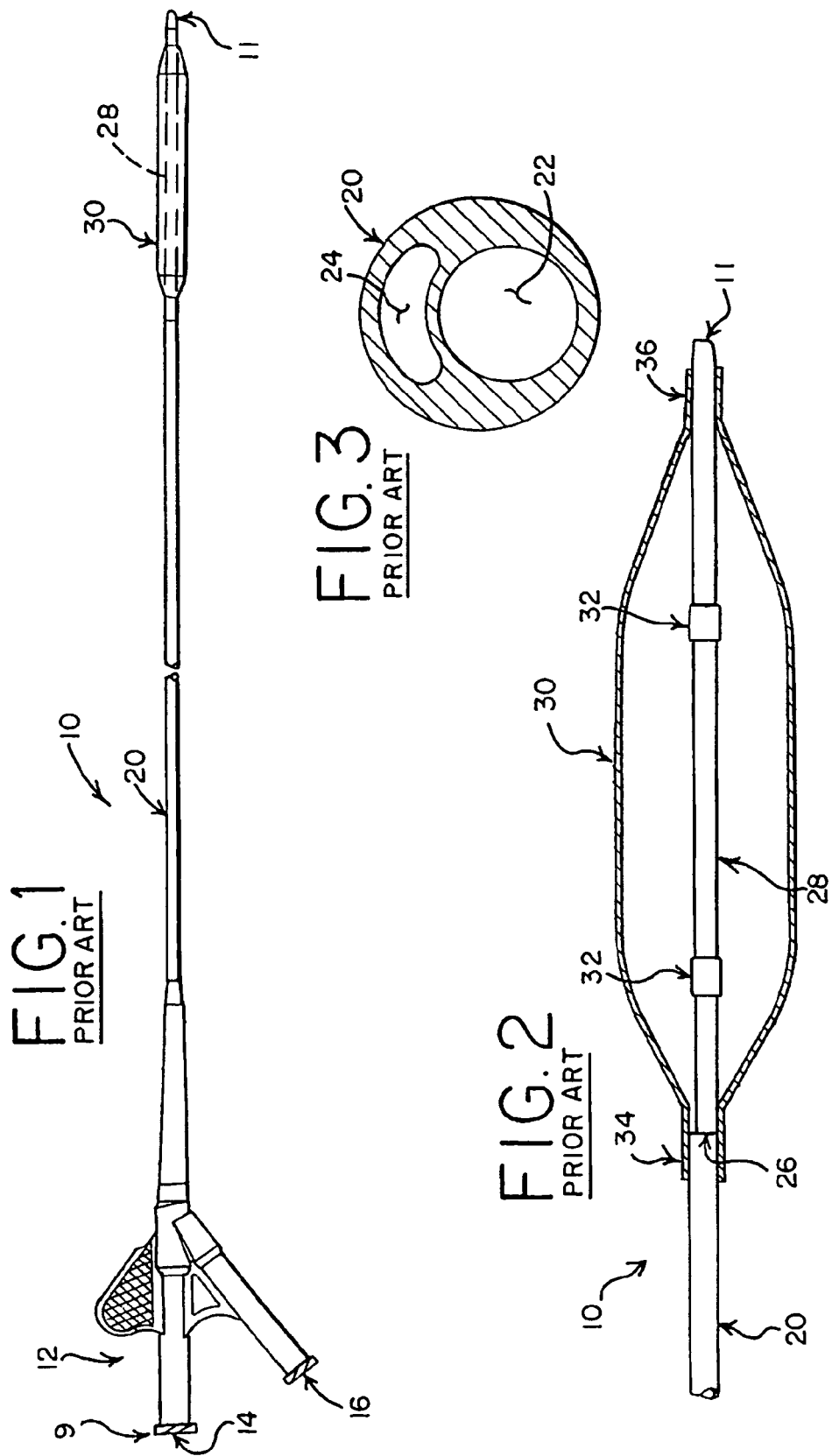

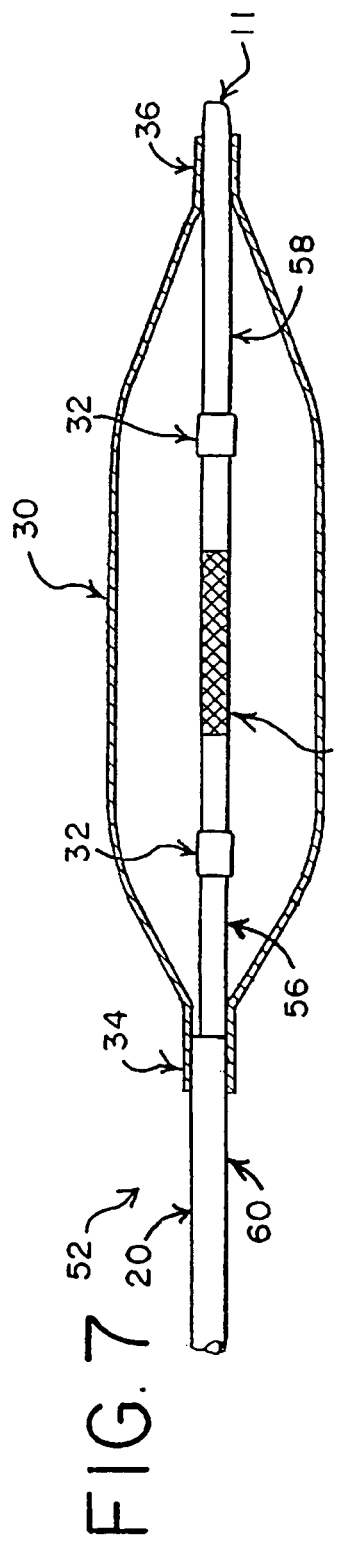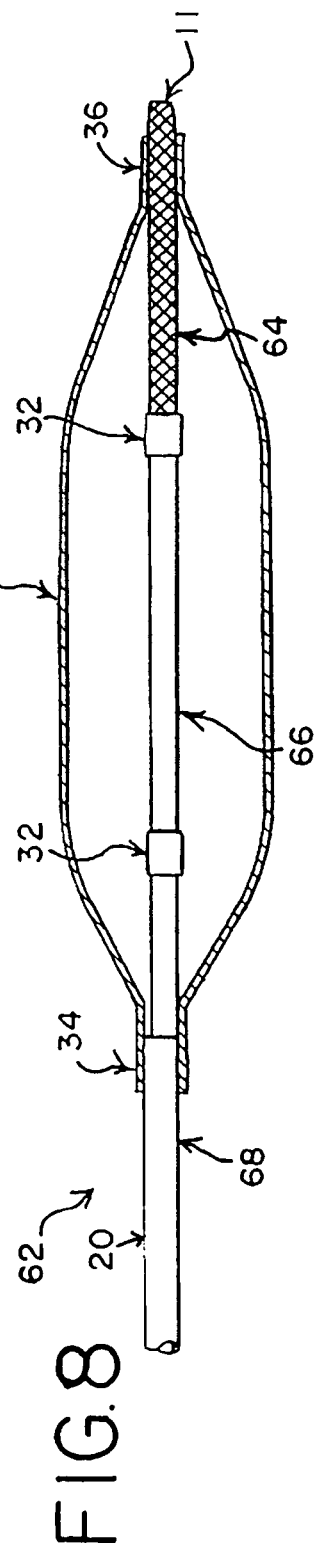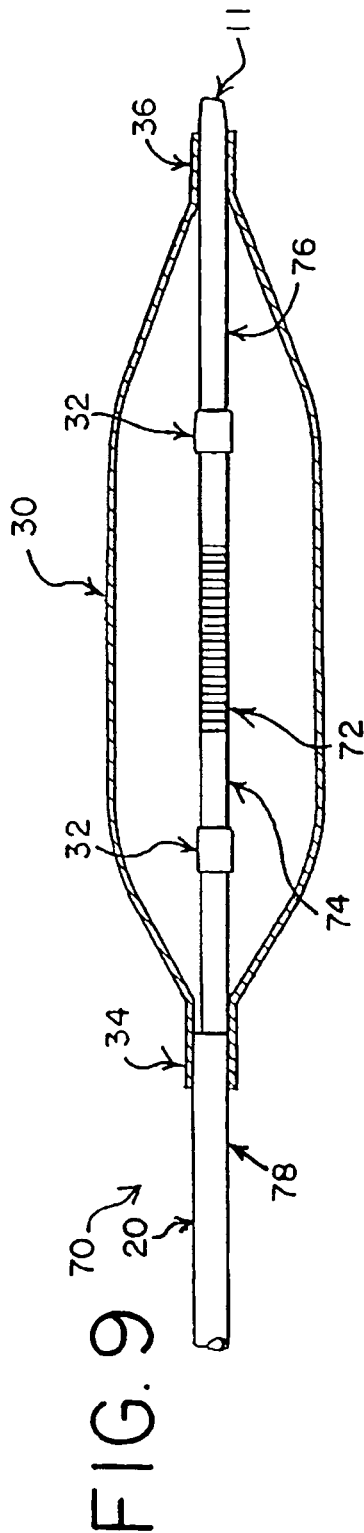

BALLOON CATHETER THAT RESISTS CURVING

This application claims priority to U.S. Provisional Application No. 60/689,451, filed Jun. 10, 2005, which is hereby incorporated by reference herein.

BACKGROUND

The present invention relates generally to intraluminal medical devices and more particularly to a balloon catheter that minimizes curving of the balloon during inflation thereof.

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, coronary angioplasty using a balloon catheter has drawn particular attention from the medical community because of the growing number of people suffering from heart problems associated with stenosis. This has lead to an increased demand for medical procedures to treat such problems. The widespread frequency of heart problems may be due to a number of societal changes, including the tendency of people to exercise less while eating greater quantities of unhealthy foods, in conjunction with the fact that people generally now have longer life spans than previous generations. Angioplasty procedures have become a popular alternative for treating coronary stenosis because angioplasty procedures are considerably less invasive than other alternatives. Traditionally, stenosis of the coronary arteries has been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for coronary artery treatments, the medical community has turned to angioplasty procedures, in combination with stenting procedures, to avoid the problems associated with traditional bypass surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the coronary artery to be treated. During this stage, the balloon is uninflated and collapsed onto the shaft of the catheter in order to present a low profile which may be passed through the arterial lumens. Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the arteries. If a stent is used, the stent is left permanently implanted in its expanded state at the desired location in the artery to provide a support structure that prevents the artery from collapsing back to its pre-dilated condition. However, the above described example is only one use for balloon catheters, and many other uses are also possible.

One disadvantage of some current balloon catheters is that they may have a tendency to curve as the balloon is inflated. Accordingly, a balloon catheter that minimizes curving of the balloon during inflation would be desirable.

BRIEF SUMMARY

Accordingly, a balloon catheter is described that minimizes the tendency of the balloon to curve as the balloon is expanded. In one embodiment, the balloon catheter has an inner shaft that is elastic. Thus, when the pressure of the inflation media inside the balloon is increased, the inner shaft may stretch longitudinally to accommodate longitudinal expansion of the balloon. As a result, the balloon tends to remain straight during inflation instead of curving. In another embodiment, the balloon catheter has an inner shaft with a corrugated portion. The corrugated portion allows the inner shaft to stretch during inflation of the balloon to minimize balloon curvature. Additional details are described below.

BRIEF DESCRIPTION OF SEVERAL VIEWS OF THE DRAWINGS

The invention may be more fully understood by reading the following description in conjunction with the drawings, in which:

FIG. 1 is a side elevational view of a prior art balloon catheter;

FIG. 2 is an enlarged cross-sectional view of the prior art balloon catheter shown in FIG. 1;

FIG. 3 is an enlarged cross-sectional view of the prior art proximal shaft shown in FIG. 1;

FIG. 7 is an enlarged cross-sectional view of another balloon catheter, showing an inner shaft made from an elastic material attached to a second proximal shaft portion and attached to a distal shaft;

FIG. 8 is an enlarged cross-sectional view of another balloon catheter, showing an inner shaft made from an elastic material attached to the distal end of the balloon; and FIG. 9 is an enlarged cross-sectional view of another balloon catheter, showing a portion of the inner shaft made from a corrugated material to resist curving of the balloon during inflation.

DETAILED DESCRIPTION

Figures 4, 5, 6:
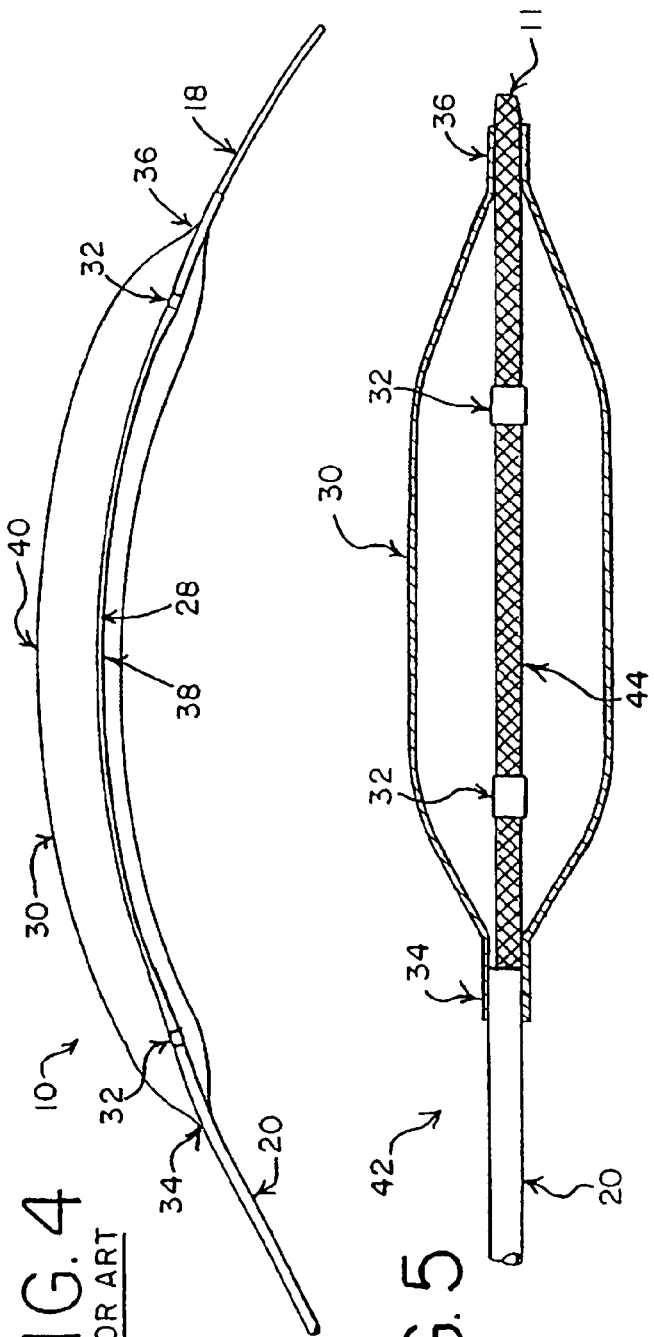
FIG. 4 is a side elevational view of the prior art balloon catheter shown in FIGS. 1 and 2, showing the balloon curved due to inflation of the balloon.
FIG. 5 is an enlarged cross-sectional view of a balloon catheter, showing an inner shaft made from an elastic material to resist curving of the balloon during inflation.
FIG. 6 is an enlarged cross-sectional view of another balloon catheter, showing an inner shaft made from an elastic material attached to a distal shaft.

Referring now to the drawings, and particularly to FIGS. 1-4, a prior art balloon catheter 10 is shown. Typically, a balloon catheter 10 has a manifold 12 at the proximal end 9 of the catheter 10 with various ports 14, 16. For example, the balloon catheter 10 that is shown has one port 14 for the guidewire 18 and one port 16 for an inflation media as further described below. The manifold 12 is attached to a proximal shaft 20 that extends toward the distal end 11 of the catheter 10. As shown in FIG. 3, the proximal shaft 20 may have two different lumens 22, 24 passing longitudinally through the proximal shaft 20. In the example shown, one lumen 22 is for the guidewire 18 and the other lumen 24 is for the inflation media. Thus, the guidewire port 14 of the manifold 12 opens to the guidewire lumen 22, and the inflation port 16 opens to the inflation lumen 24. The described manifold, ports and lumens, however, are only one example of the type of structure that may be used with a balloon catheter and many other examples are possible as well.

At the distal end 26 of the proximal shaft 20, the proximal shaft 20 may be bonded to an inner shaft 28. As used herein, the term "bonded" simply refers to the boundary between two portions and is not meant to refer to a particular technique for adhering two members together. For example, two shafts may be bonded together by gluing, heat welding, friction welding or the like. However, shafts may also be bonded together by extruding a shaft with two different portions having different shapes, material properties or other characteristics. Furthermore, two members may be attached in various other ways, including with intermediate members disposed therebetween. As shown in FIG. 2, the inner shaft 28 is smaller in diameter than the proximal shaft 20 and is shifted from the center axis of the proximal shaft 20 so that the guidewire lumen 22 of the proximal shaft 20 lines up with a matching guidewire lumen 22 extending through the inner shaft 28. Because the inner shaft 28 is smaller in diameter than the proximal shaft 20 and is shifted away from the inflation lumen 24, the inflation lumen 24 is exposed at the distal end 26 of the proximal shaft 20 to the interior of the balloon 30.

In the prior art embodiment shown in FIGS. 1-4, the inner shaft 28 extends to the distal end 11 of the catheter 10. Radiopaque bands 32 may be added to the inner shaft 28 to allow the physician to see the location of the balloon catheter 10 with visualization equipment during intraluminal procedures. The guidewire lumen 22 of the catheter 10 opens at the distal end 11 of the catheter 10 to allow the catheter 10 to pass over a guidewire 18. The inner shaft 28 is encompassed by a balloon 30, which may be used in angioplasty procedures or various other procedures. As shown, the proximal end 34 of the balloon 30 is bonded to both the proximal shaft 20 and the inner shaft 28. However, the proximal end 34 could be bonded to only the proximal shaft 20 or the inner shaft 28 as desired. The distal end 36 of the balloon 30 is bonded to the inner shaft 28. Although various materials may be used for the balloon catheter 10, nylon-based materials, such as polyether block amide (PEBA), which are biocompatible are preferred for most of the components.

As shown in FIG. 4, one problem that prior art balloon catheters 10 like the one described above may suffer from is a tendency to curve when inflation pressure is applied to the balloon 30. Typically, current balloon catheters 10 are rated for balloon pressures of approximately five to twenty atmospheres. However, it has been found that the balloon 30 of some balloon catheters 10 begins to curve as the pressure increases above about ten atmospheres. As a result, the balloon 30 forms a curved shape when inflated under pressure, with an inner apex 38 and an outer apex 40 being formed approximately along the mid-point of the length of the balloon 30. Curving of the balloon 30 generally occurs because the balloon 30 seeks to expand both radially and longitudinally as inflation media is added to the interior of the balloon 30. The inner shaft 28, however, resists longitudinal expansion of the balloon 30. As a result, the balloon 30 compensates for the longitudinal expansion by curving or bending. As shown in FIG. 4, the inner apex 38 of the curved balloon 30 may contact the inner shaft 28 and may also bend the inner shaft 28 along the shape of the inner apex 38. The direction of balloon curvature is not always predictable and may depend on various manufacturing or design characteristics and the orientation of the balloon 30 during intraluminal procedures. Although the amount of balloon curvature depends on the structure of the balloon catheter 10 and other factors, a balloon curvature of as much as 20 mm has been measured on certain models. Generally, it appears that greater degrees of curvature are experienced with balloon catheters 10 having relatively thin-walled balloons 30 that are inflated to relatively high pressures. As described above, the resulting curvature of the balloon 30 when it is inflated may have significant risks that are undesirable.

One alternative for minimizing the amount of balloon curvature in a balloon catheter is to use an inner shaft with a portion made from a material with greater elasticity than conventional inner shafts. For example, it has been determined in tests that the maximum recommended Young's modulus for the inner shaft portion is about 85 kpsi or less when the double wall thickness of the balloon is about 0.003". As those in the art well-know, double wall thickness is a measurement of two thickness of the walls of a balloon folded adjacent each other in order to make taking measurements easier. It has also been determined that the maximum recommended Young's modulus for an inner shaft portion is about 55 kpsi or less when the double wall thickness of the balloon is about 0.0025". Further, it has been determined that the maximum recommended Young's modulus for an inner shaft portion is about 25 kpsi or less when the double wall thickness of the balloon is about 0.002". Thus, it can now be seen from the described relationship that it may be desirable to decrease the Young's modulus of the inner shaft portion as the double wall thickness of the balloon is reduced. In each of these cases, it was determined that the resulting curvature of the balloon was minimal if the Young's modulus of the inner shaft portion is maintained at or below the recommended values for the particular balloons tested.

Turning now to FIG. 5, one embodiment of a balloon catheter 42 may have an inner shaft 44 bonded to the proximal shaft 20. As described above, the inner shaft 44 has a greater elasticity than conventional inner shafts. In contrast, the proximal shaft 20 may have a Young's modulus higher than the inner shaft 44. As shown, the inner shaft 44 extends from the proximal shaft 20 to the distal end 11 of the catheter 42. Thus, the guidewire lumen 22 extends through the proximal shaft 20 and inner shaft 44. The distal end 36 of the balloon 30 may be bonded to the inner shaft 44, and the proximal end 34 of the balloon 30 may be bonded to the proximal shaft 20 and the inner shaft 44 or the proximal shaft 20 alone. If desired, radiopaque bands 32 may be added to the inner shaft 44. Preferably, the inner shaft 44 as well as the inner shaft portions described below are made from a biocompatible nylon-based material.

Turning now to FIG. 6, another embodiment of a balloon catheter 46 may have an inner shaft portion 48 bonded to the proximal shaft 20 and a distal shaft 50. As described above, the inner shaft portion 48 has a greater elasticity than conventional inner shafts. In contrast, the proximal shaft 20 and distal shaft 50 may have a Young's modulus higher than the inner shaft portion 48. As shown, the inner shaft portion 48 extends from the proximal shaft 20 to the distal shaft 50. The distal shaft 50 is bonded to the inner shaft portion 48 and extends to the distal end 11 of the catheter 46. Thus, the guidewire lumen 22 extends through the proximal shaft 20, inner shaft portion 48 and distal shaft 50. The distal end 36 of the balloon 30 may be bonded to the distal shaft 50, and the proximal end 34 of the balloon 30 may be bonded to the proximal shaft 20 and the inner shaft portion 48 or the proximal shaft 20 alone. If desired, radiopaque bands 32 may be added to the inner shaft portion 48 and/or the distal shaft 50.

Turning now to FIG. 7, another embodiment of a balloon catheter 52 may have an inner shaft portion 54 bonded to a second proximal shaft portion 56 and a distal shaft 58. In contrast, the second proximal shaft portion 56 and distal shaft 58 may have a Young's modulus higher than the inner shaft portion 54. As shown, the proximal shaft 20 may be made of a first proximal shaft portion 60 and a second proximal shaft portion 56. The first proximal shaft portion 60 may have a larger diameter than the second proximal shaft portion 56 in order to expose the inflation lumen 24 to the interior of the balloon 30 as described above. The distal shaft 58 extends to the distal end 11 of the catheter 52. Thus, the guidewire lumen 22 extends through the first proximal shaft portion 60, second proximal shaft portion 56, inner shaft portion 54 and distal shaft 58. The distal end 36 of the balloon 30 may be bonded to the distal shaft 58, and the proximal end 34 of the balloon 30 may be bonded to the first and second proximal shaft portions 60, 56 or to the first proximal shaft portion 60 alone. If desired, radiopaque bands 32 may be added to the second proximal shaft portion 56 and the distal shaft 58.

Turning now to FIG. 8, another embodiment of a balloon catheter 62 may have an inner shaft portion 64 bonded to a second proximal shaft portion 66. In contrast, the second proximal shaft portion 66 may have a Young's modulus higher than the inner shaft portion 64. As described above, the inner shaft portion 64 has a greater elasticity than conventional inner shafts. As shown, the proximal shaft 20 may be made of a first proximal shaft portion 68 and a second proximal shaft portion 66. The first proximal shaft portion 68 may have a larger diameter than the second proximal shaft portion 66 in order to expose the inflation lumen 24 to the interior of the balloon 30 as described above. The inner shaft portion 64 extends to the distal end 11 of the catheter 62. Thus, the guidewire lumen 22 extends through the first proximal shaft portion 68, second proximal shaft portion 66 and inner shaft portion 64. The distal end 36 of the balloon 30 may be bonded to the inner shaft portion 64, and the proximal end 34 of the balloon 30 may be bonded to the first and second proximal shaft portions 68, 66. If desired radiopaque bands 32 may be added to the second proximal shaft portion 66 and/or the inner shaft portion 64.

Turning now to FIG. 9, another embodiment of a balloon catheter 70 may have an inner shaft portion 72 bonded to a second proximal shaft portion 74 and a distal shaft 76. In this embodiment, the inner shaft portion 72 may be made of a corrugated material. A corrugated material may be made with ridges that are folded against each other or with other constructions that are known. Thus, the corrugated material is designed specifically to stretch in length when a longitudinal force is applied. As a result, the corrugated material of the inner shaft portion 72 may stretch to minimize curving of the balloon 30 upon inflation. In contrast, the second proximal shaft portion 74 and the distal shaft 76 are made from non-corrugated materials that require significantly greater force to cause stretching. Corrugations may be integrally formed in a one-piece inner shaft so that a separate section of corrugated tubing is not required or a separate section of corrugated material may be used. As shown, the proximal shaft 20 may be made of a first proximal shaft portion 78 and a second proximal shaft portion 74. The first proximal shaft portion 78 may have a larger diameter than the second proximal shaft portion 74 in order to expose the inflation lumen 24 to the interior of the balloon 30 as described above. The distal shaft 76 extends to the distal end 11 of the catheter 70. Thus, the guidewire lumen 22 extends through the first proximal shaft portion 78, second proximal shaft portion 74, inner shaft portion 72 and distal shaft 76. The distal end 36 of the balloon 30 may be bonded to the distal shaft 76, and the proximal end 34 of the balloon 30 may be bonded to the first and second proximal shaft portions 78, 74. If desired, radiopaque bands 32 may be added to the second proximal shaft portion 74 and the distal shaft 76.

The advantages of the invention are now apparent. An inner shaft made from an elastic material or corrugated material may allow the length of the inner shaft to stretch when axial force is applied to the inner shaft. Thus, when inflation media fills the balloon and causes the balloon to expand longitudinally due to pressure, the inner shaft stretches lengthwise to match the longitudinal expansion of the balloon. As a result, the inner shaft does not resist longitudinal expansion of the balloon like prior art balloon catheters. Therefore, the tendency of the balloon to curve as it is inflated may be eliminated or significantly minimized.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein.

We claim:

1. A balloon catheter for intraluminal medical treatment, comprising:
    a catheter comprising a proximal shaft portion and an inner shaft portion attached to said proximal shaft portion, said inner shaft portion being disposed distal from said proximal shaft portion, wherein a first lumen extends through at least part of said proximal shaft portion and a second lumen extends through at least said proximal shaft portion and said inner shaft portion;
    a balloon comprising a proximal end and a distal end, said proximal end and said distal end being attached to said catheter, said balloon thereby encompassing at least a part of said inner shaft portion between said proximal end and said distal end, and said first lumen being exposed to an interior of said balloon;
    wherein said balloon is collapsible onto said catheter to facilitate intraluminal insertion of said balloon and said catheter into a body cavity, said catheter being threadable through a body lumen by extending a guidewire through said second lumen, said balloon thereby being inflatable to dilate said body cavity by passing an inflation media through said first lumen into said interior of said balloon; and
    wherein a double wall thickness of said balloon is about 0.003" or less and said inner shaft portion is made from a non-corrugated elastic material with a Young's modulus low enough to permit said inner shaft portion to stretch as said balloon is inflated to minimize curving of said balloon due to a pressure of said inflation media.

2. The balloon catheter according to claim 1, wherein said inner shaft portion is smaller in diameter than said proximal shaft portion, said inner shaft portion being bonded to only part of a cross-sectional area of said proximal shaft portion, said first lumen opening at an unexposed part of said cross-sectional area and thereby being exposed to said interior of said balloon.

3. The balloon catheter according to claim 1, wherein said proximal shaft portion, said inner shaft portion and said balloon are made from a biocompatible nylon-based material.

4. The balloon catheter according to claim 1, wherein at least two radiopaque markers are attached to said inner shaft portion.

5. The balloon catheter according to claim 1, wherein said inner shaft portion is bonded to said proximal shaft portion and said distal end of said balloon is attached to said inner shaft portion.

6. The balloon catheter according to claim 5, wherein said inner shaft portion extends to a catheter distal end.

7. The balloon catheter according to claim 6, wherein said proximal end of said balloon is attached to at least part of said proximal shaft portion.

8. The balloon catheter according to claim 1, further comprising a distal shaft portion attached to said inner shaft portion, said distal shaft portion being disposed distal from said inner shaft portion and said second lumen extending through said distal shaft portion, wherein said distal end of said balloon is attached to said distal shaft portion, said distal shaft portion being made from a material with a Young's modulus higher than said inner shaft portion.

9. The balloon catheter according to claim 8, wherein said proximal end of said balloon is attached to at least part of said proximal shaft portion.

10. The balloon catheter according to claim 1, wherein said proximal shaft portion comprises a first proximal shaft portion and a second proximal shaft portion, said balloon encompassing at least a part of said second proximal shaft portion between said proximal end and said distal end, and said second proximal shaft portion being attached to said inner shaft portion, said inner shaft portion being disposed distal from said second proximal shaft portion, wherein said second proximal shaft portion is made from a material with a Young's modulus higher than said inner shaft portion.

11. The balloon catheter according to claim 10, further comprising a distal shaft portion attached to said inner shaft portion, said distal shaft portion being disposed distal from said inner shaft portion and said second lumen extending through said distal shaft portion, wherein said distal end of said balloon is attached to said distal shaft portion, said distal shaft portion being made from a material with a Young's modulus higher than said inner shaft portion.

12. The balloon catheter according to claim 11, wherein said first proximal shaft portion is larger in diameter than said second proximal shaft portion, said proximal end of said balloon being attached to at least part of said first proximal shaft portion.

13. The balloon catheter according to claim 1, wherein said distal end of said balloon is attached to said inner shaft portion.

14. The balloon catheter according to claim 13, wherein said proximal shaft portion comprises a first proximal shaft portion and a second proximal shaft portion, said balloon encompassing at least a part of said second proximal shaft portion between said proximal end and said distal end, and said second proximal shaft portion being attached to said inner shaft portion, said inner shaft portion being disposed distal from said second proximal shaft portion, wherein said second proximal shaft portion is made from a material with a Young's modulus higher than said inner shaft portion.

15. The balloon catheter according to claim 14, wherein said first proximal shaft portion is larger in diameter than said second proximal shaft portion, said proximal end of said balloon being attached to at least part of said first proximal shaft portion, and said inner shaft portion extends to a catheter distal end.

16. The balloon catheter according to claim 1, wherein said double wall thickness of said balloon is about 0.003" and said elastic material has a Young's modulus of about 85 kpsi or less.

17. The balloon catheter according to claim 1, wherein said double wall thickness of said balloon is about 0.0025" and said elastic material has a Young's modulus of about 55 kpsi or less.

18. The balloon catheter according to claim 1, wherein said double wall thickness of said balloon is about 0.002" and said elastic material has a Young's modulus of about 25 kpsi or less.

19. The balloon catheter according to claim 1, wherein a maximum Young's modulus of said elastic material is proportional to said double wall thickness of said balloon according to the following relationship:

| Double Wall | |
|---|---|
| Thickness | Young's Modulus |
| 0.003" | 85 kpsi |
| 0.0025" | 55 kpsi |
| 0.002" | 25 kpsi. |

\* \* \* \* \*

UNITED STATES PATENT AND TRADEMARK OFFICE
CERTIFICATE OF CORRECTION

PATENT NO. : 8,292,912 B2  
APPLICATION NO. : 11/450912  
DATED : October 23, 2012  
INVENTOR(S) : David G. Burton et al.

Page 1 of 1

It is certified that error appears in the above-identified patent and that said Letters Patent is hereby corrected as shown below:

<u>In the Claims</u>

In column 8, after claim 19, line 36, replace the entire table with the following table:

| Double Wall Thickness | Young's Modulus |
|---|---|
| 0.003" | 85 kpsi |
| 0.0025" | 55 kpsi |
| 0.002" | 25 kpsi |

--.

Signed and Sealed this
Fifth Day of March, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,292,912 B2 | Page 1 of 1 |
| APPLICATION NO. | : 11/450912 | |
| DATED | : October 23, 2012 | |
| INVENTOR(S) | : Burton et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1392 days.

Signed and Sealed this
Twenty-eighth Day of October, 2014

Michelle K. Lee
*Deputy Director of the United States Patent and Trademark Office*